United States Patent [19]
Carlson et al.

[11] Patent Number: 5,820,600
[45] Date of Patent: Oct. 13, 1998

[54] ADJUSTABLE INTRODUCER VALVE

[75] Inventors: John Carlson, Mountain View; Tellis Hartridge, San Jose; Andrew Lee, Cupertino; Steve Masterson, San Francisco; Mike Orth, Morgan Hill; Craig Tsuji, Santa Clara, all of Calif.

[73] Assignee: Innerdyne, Inc., Sunnyvale, Calif.

[21] Appl. No.: 649,144

[22] Filed: May 14, 1996

[51] Int. Cl.⁶ .................................................. A61M 5/00
[52] U.S. Cl. ...................... 604/167; 251/149.2; 604/256
[58] Field of Search ............................ 251/149.2, 149.8; 604/164, 167, 169, 246, 256

[56] References Cited

U.S. PATENT DOCUMENTS

| | | | |
|---|---|---|---|
| 3,685,786 | 8/1972 | Woodson | 251/4 |
| 4,177,814 | 12/1979 | Knepshield et al. | 128/348 |
| 4,211,214 | 7/1980 | Chikashige | 128/4 |
| 4,538,594 | 9/1985 | Boebel et al. | 128/6 |
| 4,649,904 | 3/1987 | Krauter et al. | 128/6 |
| 4,809,679 | 3/1989 | Shimonaka et al. | 238/4 |
| 4,874,364 | 10/1989 | Morris et al. | 604/35 |
| 4,920,953 | 5/1990 | McGown | 128/4 |
| 5,048,508 | 9/1991 | Storz | 128/4 |
| 5,127,626 | 7/1992 | Hilal et al. | 251/149.1 |
| 5,167,636 | 12/1992 | Clement | 604/167 |
| 5,209,219 | 5/1993 | Hollobaugh | 128/4 |
| 5,209,737 | 5/1993 | Ritchart et al. | 604/167 |
| 5,211,633 | 5/1993 | Stouder, Jr. | 604/167 |
| 5,221,264 | 6/1993 | Wilk et al. | 604/167 |
| 5,304,143 | 4/1994 | Green et al. | 604/167 |
| 5,308,336 | 5/1994 | Hart et al. | 604/167 |
| 5,334,164 | 8/1994 | Guy et al. | 604/248 |
| 5,338,313 | 8/1994 | Mollenauer et al. | 604/249 |
| 5,354,280 | 10/1994 | Haber et al. | 604/167 |
| 5,385,552 | 1/1995 | Haber et al. | 604/167 |
| 5,385,553 | 1/1995 | Hart et al. | 604/167 |
| 5,389,081 | 2/1995 | Castro | 604/167 |
| 5,391,153 | 2/1995 | Haber et al. | 604/167 |
| 5,397,335 | 3/1995 | Gresl et al. | 606/185 |
| 5,407,433 | 4/1995 | Loomas | 604/167 |
| 5,411,483 | 5/1995 | Loomas et al. | 604/167 |
| 5,431,676 | 7/1995 | Dubrul et al. | 606/185 |
| 5,512,053 | 4/1996 | Pearson et al. | 604/167 |
| 5,607,397 | 3/1997 | Stephens et al. | 604/167 |
| 5,657,963 | 8/1997 | Hinchliffe et al. | 251/149.1 |

FOREIGN PATENT DOCUMENTS 0 567 141 A2   4/1993   European Pat. Off. ....... A61M 39/00

*Primary Examiner*—Corrine M. McDermott
*Attorney, Agent, or Firm*—Townsend and Townsend and Crew LLP

[57] ABSTRACT

An adjustable pnemostasis valve and method for providing a fluid seal around the periphery of endoscopic viewing scopes and instruments having a wide variety of cross-sectional sizes. The valve (8) comprises a first valve member (50) having an opening for receiving an elongated object, such as a percutaneous access device, viewing scope or an endoscopic instrument, and a flexible membrane (60) defining an aperture substantially aligned with the opening in the first valve member. A second valve member (40) is coupled to the flexible membrane for moving the membrane relative to the first valve member. As the membrane is moved by the second valve member, the size of the aperture varies so that the membrane can accommodate various sized instruments.

23 Claims, 3 Drawing Sheets

ADJUSTABLE INTRODUCER VALVE

BACKGROUND OF THE INVENTION

1. Field of the Invention

The present invention relates generally to apparatus and methods for providing percutaneous access to an internal operative site during a surgical procedure. More particularly, the present invention relates to an adjustable trocar valve for accommodating viewing scopes and instruments having a wide variety of cross-sectional shapes and sizes.

Minimally invasive surgical procedures are typically performed by penetrating the patient's skin with small-diameter access tubes, usually referred to as trocars, and opening the trocars within a patient's body cavity. A viewing scope is introduced through one such trocar and the surgeon operates using instruments introduced through other appropriately placed trocars while viewing the operative site on a video monitor connected to the viewing scope. Minimally invasive or endoscopic procedures generally require sealing of the instruments inserted into the body, i.e., provisions must be made to ensure that fluids do not enter or exit the body through the endoscopic incision. For example, in procedures in the abdominal area (laparoscopic procedures), the patient's abdominal region is typically insufflated with pressurized carbon dioxide or nitrogen gas to raise the abdominal wall and to create sufficient operating space within the abdomen. Trocars used in laparoscopic procedures generally include a valve at their proximal end to allow passage of the scope or surgical instrument while inhibiting leakage of the insufflating gas or other body fluids.

The design of suitable trocar valves involves specialized considerations, particularly the design of trocar valves used in laparoscopic procedures in a pressurized environment. The trocar valves used in these procedures should be readily sealable to inhibit the leakage of gas and other fluids from the abdomen or other body cavities. In addition, it would be desirable if a single trocar could accommodate and provide a seal for instruments having a wide variety of cross-sectional shapes and sizes. This would reduce the number of incisions required for a surgical procedure, thereby minimizing trauma to the patient.

In the past, accommodation of various sized instruments has been met by providing trocars having different fixed diameters. Often, the surgeon would introduce the largest sized trocar, usually 10 to 12 mm, which can then accommodate most or all instruments using a rubber adapter. While such an approach is feasible, the introduction of larger sized trocars increases the trauma and the risk of injury to the patient than would be the case if smaller trocars were used. In addition, the rubber adapter typically does not provide an adequate fluid seal for smaller instruments.

Trocar valves have been designed with inner seals that can accommodate various sized instruments. Typically, these seals comprise a one-way elastomeric member(s) that allows instruments to pass through, while inhibiting fluid leakage between the instrument shaft and the seal. For example, one such elastomeric member comprises an elastomeric plug having crossed slits designed to allow instruments to pass through the slits in the distal direction. Endoscopic instruments are introduced from the proximal end of the trocar through the crossed slits, forcing the elastomeric member to open and allow passage of the instrument to the percutaneous incision. The elastomeric plug is biased against the instrument periphery to create a fluid seal.

The one-way elastomeric seals described above have a number of drawbacks. For example, these types of seals typically do not assume a shape that corresponds with the instrument's cross-sectional shape (usually circular) after the instrument has penetrated through the seal. Accordingly, fluid pressure within the body cavity may cause leakage of gases or other bodily fluids between the elastomeric seal and the instrument. Another drawback with these types of seals is that the bias force applied to the instrument by the seal creates frictional resistance to movement of the instrument, which makes it more difficult for the surgeon to manipulate the instrument within the patient's body. In addition, larger diameter instruments tend to force the elastomeric seal radially outward further than smaller diameter instruments, thereby increasing the bias force against these instruments. The increased bias force leads to increased friction, making it even more difficult for the surgeon to manipulate larger diameter instruments during the surgical procedure.

Another drawback with existing trocars is that the cannula shaft typically has an axial lumen with a diameter at least as large as the largest instrument that will pass therethrough (i.e., typically around 10–12 mm). Thus, when the surgeon introduces and/or manipulates smaller diameter instruments through the axial lumen of the cannula, these instruments will pivot or move transversely within this lumen. Pivotal or transverse movement of the instrument causes lateral pressure to be applied against the elastomeric seal within the trocar valve. This lateral pressure against the seal may allow gases or other fluids to leak between the seal and the opposite side of the instrument shaft.

For these and other reasons, it would be desirable to provide trocars suitable for use in laparoscopic and other minimally invasive procedures which can accommodate a wide variety of instrument sizes. It would be desirable if these trocars incorporated adjustable seals designed to accommodate various sized instruments and to assume a shape generally corresponding with the cross-sectional shape of the instruments passing therethrough to facilitate the formation of a fluid-tight seal around the instrument periphery. In addition, the adjustable seals should be designed to minimize the frictional resistance against instruments passing therethrough to facilitate manipulation of the instruments within the patient's body by the surgeon. Further, it would be desirable to reduce or eliminate lateral pressure applied against the trocar seal by instruments pivoting or otherwise moving within the trocar shaft to thereby minimize fluid leakage through the trocar valve.

2. Description of the Background Art

U.S. Pat. Nos. 5,354,280, 5,385,552 and 5,391,153 to Haber describe trocars having seals for accommodating various sized instruments. The seals comprise a plurality of elastomeric elements biased toward each other within the trocar shaft. The seals are arranged so that pressure from the proximal end will force the seals open to allow instruments to pass through. U.S. Pat. Nos. 5,338,313 and 5,167,636 describe trocar valves with radially compressible sealing bodies for receiving various sized instruments.

U.S. Pat. No. 5,304,143 to Green teaches a valve assembly comprising first and second valves for allowing the passage of instruments therethrough. The first valve comprises a resilient material configured to engage the outer surface of the instrument in a fluid tight manner. The second valve includes a pair of manually operated clamps for opening and closing the second valve. U.S. Pat. No. 5,127,626 to Hilal describes a trocar valve having spring biased cams for radially compressing sealing members into sealing engagement with instruments extending through an axial passage of the trocar.

U.S. Pat. Nos. 5,407,433 and 5,407,433 to Loomas describe a gas-tight seal for accomodating surgical instruments with varying diameters. The seal can be moved laterally in response to lateral movement of the instrument. U.S. Pat. No. 5,397,335 to Gresl discloses a trocar assembly having removable adapter seals for accomodating instruments of various sizes.

SUMMARY OF THE INVENTION

The present invention provides methods and apparatus for providing percutaneous access to an internal operative site during a surgical procedure. In particular, the invention provides an adjustable pnemostasis valve for providing a fluid seal around the periphery of endoscopic viewing scopes and instruments having a wide variety of cross-sectional sizes. The valve comprises a first valve member having an opening for receiving an elongated object, such as an insufflation needle, obturator, viewing scope or an endoscopic instrument, and a flexible membrane defining an aperture substantially aligned with the opening in the first valve member. A second valve member is coupled to the flexible membrane for moving the membrane relative to the first valve member. As the membrane is moved by the second valve member, the size of the aperture varies so that the membrane can accommodate various sized instruments.

The flexible membrane is constructed of a resilient, elastomeric material suitable for sealing various sized instruments, such as urethane, rubber, silicone or the like. Movement of the second valve member either stretches or relaxes the membrane to thereby change the size of the aperture. Preferably, the membrane has an annular shape with an outer peripheral edge and an inner portion that defines a circular, central aperture for accommodating cylindrical instruments. Movement of the second valve member stretches or relaxes the outer peripheral edge of the membrane, thereby enlarging or reducing the size, i.e., cross-sectional area, of the aperture. Unlike many prior art valves, the membrane aperture will generally retain its circular shape when the area of the aperture varies so that the membrane conforms to the cylindrical instruments passing therethrough. This helps to minimize fluid leakage between the membrane and the instruments.

The membrane is configured to naturally provide a gas-tight seal around the periphery of instruments (i.e., the membrane is not directly biased against the outer surface of the instrument). Usually, the membrane will be suitably stretched or relaxed by the second valve member so that the aperture has a diameter slightly less than the outer diameter of the instrument passing therethrough to provide a gas seal against the instrument. Preferably, the aperture diameter will only be slightly less than the instrument diameter, (e.g., on the order of about 0.1 to 0.2 mm) to minimize frictional resistance between the instrument and the membrane, thereby facilitating manipulation of the instrument by the surgeon. In addition, since the aperture size is changed by the second valve member (and not by the instrument forcing the aperture radially outward), the membrane will apply substantially the same amount of inward force against smaller and larger sized instruments. Therefore, the frictional resistance between the instruments and the membrane will be substantially the same for different sized instruments so that the surgeon does not encounter different degrees of friction for each instrument during surgical procedures.

In a specific configuration, the second valve member is a collar threadably coupled to the outer surface of a hollow tube (the first valve member) having a proximal opening for receiving viewing scopes, instruments and the like. The outer edge of the membrane is attached to the collar, and the inner portion of the membrane stretches over the top of the hollow tube to cover a portion of the proximal opening. Rotation of the collar axially moves the collar and the outer edge of the membrane relative to the hollow tube to either stretch or relax the inner portion of the membrane. To enlarge the aperture, for example, the surgeon rotates the collar so that the collar and the outer edge of the membrane move distally relative to the hollow tube. This stretches the inner portion of the membrane radially outward from the center of the proximal opening, thereby enlarging the aperture to receive larger instruments. Likewise, rotating the collar in the opposite direction will reduce the size of the aperture for receiving smaller instruments.

In one aspect of the invention, the valve is attached to the proximal end of a cannula shaft to form part of an introducer assembly, such as a trocar or a radially expandable introducer, for introducing instruments and viewing scopes through a percutaneous penetration into a patient's body. The valve may further include an alignment mechanism that inhibits non-axial (transverse) movement of the instruments relative to the membrane during insertion and manipulation of the instruments by the surgeon. Transversely securing the instruments to the membrane reduces the lateral pressure that may be applied by the instruments against the membrane when these instruments are pivoted or otherwise moved transversely within the cannula shaft. Reduction of the lateral pressure minimizes leakage through the valve during the surgical procedure. The valve is particularly useful in combination with radially expandable dilation devices, such as those described in U.S. Pat. No. 5,431,676, the full disclosure of which is incorporated herein by reference. The valve may also be useful with devices available under the STEP™ Cannula and Obturator with Radially Expandable Sleeve tradename from Innerdyne Medical, Sunnyvale, Calif. 94089.

In one aspect of the invention, the valve is pivotally coupled to the cannula shaft so that the membrane will rotate in response to rotation of an instrument extending through the shaft. Preferably, the valve is gimballed to the cannula shaft for rotation in any direction about a plane transverse to the shaft axis. This allows the valve to rotate in any direction about the shaft in response to pivotal movement of the instrument relative to the shaft. Consequently, the valve will pivot with the instrument to minimize lateral pressure applied by the instrument against the membrane.

In another aspect of the invention, the valve further includes means for securing a proximal portion of the instrument at or near the center of the membrane. Preferably, the securing means comprises one or more holding members coupled to the first valve member for preventing transverse movement of the instrument relative to the membrane, while allowing axial movement. The holding members are configured to moved radially inward and outward to accommodate various sized instruments.

Other features and advantages of the invention will appear from the following description in which the preferred embodiment has been set forth in detail in conjunction with the accompanying drawings.

DESCRIPTION OF THE SPECIFIC EMBODIMENTS

Figure 1:
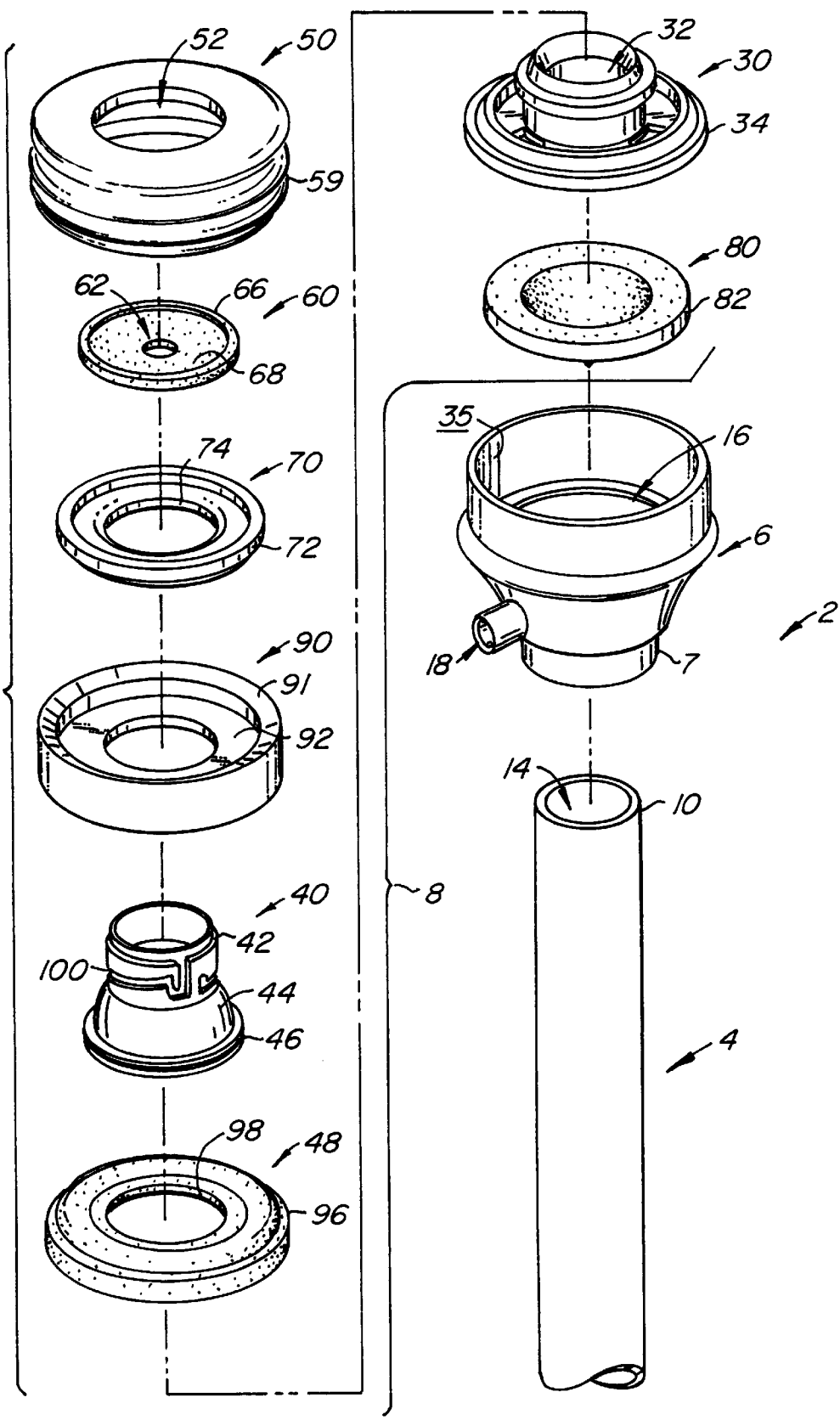
FIG. 1 is an exploded view of a representative trocar incorporating a valve assembly according to the present invention.

The present invention is useful for introducing elongate objects through percutaneous penetrations into a variety of target locations within a patient's body for a variety of purposes. Such purposes include drainage, intra-organ drug administration, feeding, perfusion, aspiration, and the like, most usually being the introduction of viewing scopes and surgical instruments for use in minimally invasive procedures, such as laparoscopy, thoracoscopy, arthroscopy and the like.

The valve assembly of the present invention will typically be used in conjunction with an introducer assembly, such as a trocar or a radially expandable introducer, for providing percutaneous access to an internal operative site during a surgical procedure. Usually, the introducer includes an elongate cannula having an axial lumen for delivering instruments and viewing scopes through a port, and an obturator, which is initially present in the cannula and which facilitates penetration of the cannula through the patient's skin. After penetrating the patient's skin, the obturator is removed to provide a port for access into a body cavity. The length of the cannula will vary depending on the intended usage, but will generally be in the range of 10 cm to 25 cm. For laparoscopic procedures, the length will usually be in the range of about 10 to 20 cm, typically being in the range of about 10 cm to 15 cm. For thoracoscopic procedures, the length will generally be shorter, typically having a length in the range of 5 to 10 cm.

The introducer will usually include a handle or cannula hub coupled to the proximal end of the cannula for facilitating manipulation of the cannula by the surgeon. The handle usually includes an inner cavity fluidly coupled to the axial lumen of the cannula and a port for introducing or venting insufflation gas, irrigation, aspiration and the like, to and from the patient's body. The valve assembly of the present invention is coupled to or incorporated within the handle for sealingly receiving instruments passing through the cannula shaft and into the patient. The present invention will find particular use with radially expandable introducers, such as the STEP™ introducer from Innerdyne Medial, Sunnyvale, Calif. 94089, as well was with conventional trocars commercially available from suppliers such as United States Surgical Corp., Norwalk, Conn.; Endomed division of Cooper Surgical Inc., Shelton, Conn.; and Dexide, Inc., Fort Worth, Tex.

The valve assembly of the present invention generally includes first and second valve members and a flexible membrane. The first and second valve members are movable relative to each other to change the shape of the membrane to provide a peripheral seal about instruments and viewing scopes having a wide variety of cross-sectional shapes and diameters. The valve members can be moved manually by the surgeon or the valve assembly may include an actuator and a drive mechanism for automatically moving the valve members. Preferably, the valve members will be configured to move between discrete settings, with each setting corresponding to a different sized instrument, such as a 5 mm or 12 mm diameter instrument. The valve assembly may further include means for displaying the instrument setting to the surgeon.

The flexible membrane is constructed of a resilient elastomeric material which is sufficiently resilient to accommodate and provide a fluid seal against the periphery of instruments of varying diameters. The membrane may comprise a variety of shapes, but is preferably a thin, annular membrane having a central, circular aperture for receiving substantially cylindrical instruments. The membrane will be capable of being stretched radially outward so that the diameter of the central aperture can be enlarged at least 1.5 to 4 times its original diameter. The valve members are configured to symmetrically stretch the outer edge of the membrane so that the central aperture substantially maintains a circular shape in the enlarged configurations, which minimizes fluid leakage through the membrane. Of course, the membrane can have an aperture with a shape other than circular, such as square, rectangular, C-shaped, etc., to accommodate instruments or scopes having shapes other than cylindrical. Membrane is constructed of a material that will generally retain its sealing properties after being stretched and then relaxed back into its natural configuration. Suitable materials for the membrane are silicone, rubber, urethane and the like.

The membrane is suitably coupled to the first and second valve members so that it will provide a gas-tight seal around the periphery of an instrument passing through the aperture. This seal will preferably result from the aperture having a slightly smaller inner diameter than the outer diameter of the instrument. The difference in diameters will preferably be large enough to create a suitable gas seal and small enough to minimize friction between the instrument and the membrane. The aperture will usually have an inner diameter of about 0.1 to 3.0 mm less than the outer diameter of the instrument passing therethrough. The instruments will typically have diameters ranging from about 5 mm to about 12 mm. Accordingly, the valve members will be configured to stretch or relax the membrane so that the aperture has a diameter from about 2.5 mm to 9.0 mm.

The valve assembly of the present invention will preferably include an alignment mechanism for preventing or at least inhibiting non-axial or transverse movement of instruments relative to the membrane. This reduces the lateral pressure that may be applied by the objects against the membrane when these objects are pivoted or otherwise moved relative to the valve and the cannula shaft. Reduction of the lateral pressure minimizes leakage through the valve during the surgical procedure.

In one configuration, the alignment mechanism comprises a device for pivoting the valve assembly relative to the handle of the introducer in response to pivotal movement of the instrument shaft. In this manner, the valve assembly will move with the instrument so that the instrument does not apply lateral pressure against a portion of the membrane when the instrument is manipulated or otherwise pivoted relative to the cannula. In another configuration, valve assembly is fixed to the handle and the alignment mechanism comprises means for securing the instrument at or near the center of the membrane, such as a plurality of elongate holding members. The holding members preferably extend radially inward to define a central gap at the membrane center for receiving the instruments. In this configuration, the holding members are capable of being pivoted or otherwise moved to change the size of the central gap for various sized instruments.

Referring now to the figures, an exemplary introducer assembly 2 constructed in accordance with the present invention will be described. As shown in FIG. 1, introducer assembly 2 generally includes an elongate shaft or cannula 4, a handle 6 and a valve assembly 8. Cannula 4 has a proximal end 10, a distal end (not shown) and an axial lumen 14 therebetween for receiving elongate objects, such as an endoscope and/or surgical instruments for performing a surgical procedure within the patient's body. Introducer assembly 2 will also include access device(s) for penetrating the patient's skin and providing a port for access into a body cavity, such as an obturator (not shown), an insufflation needle and/or a mechanism for radially expanding a penetration in the patient's skin. The access device(s) can be used to introduce or withdraw fluids, particularly being used for performing the initial stages of insufflation. One suitable access device for use with the present invention is described in commonly assigned U.S. Pat. No. 5,431,676 to Dubrul et al., the complete disclosure of which is incorporated herein by reference.

Figure 2:
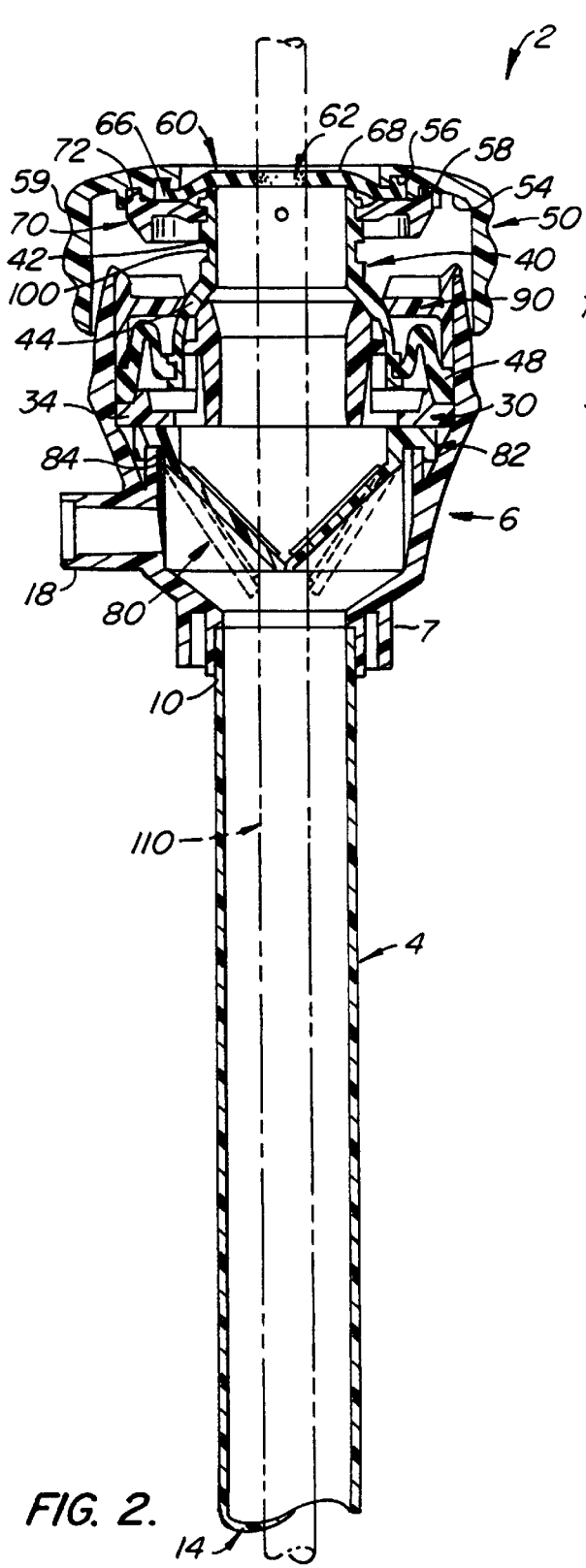
FIG. 2 is a cross-sectional view of the trocar assembly of FIG. 1 illustrating the valve assembly accommodating a 5 mm instrument.

As shown in FIG. 2, handle 6 includes a distal hub 7 attached to proximal end 10 of cannula 4. Handle 6 defines an inner cavity 16 for housing a portion of valve assembly 8 and for permitting passage of the access device(s), an endoscope and/or surgical instruments through handle 6 to axial lumen 14 of cannula 4. Handle 6 includes a port or stopcock 18 extending radially outward from cavity 16 for permitting introduction or venting of insufflation gas, irrigation, aspiration and the like.

Figure 3:
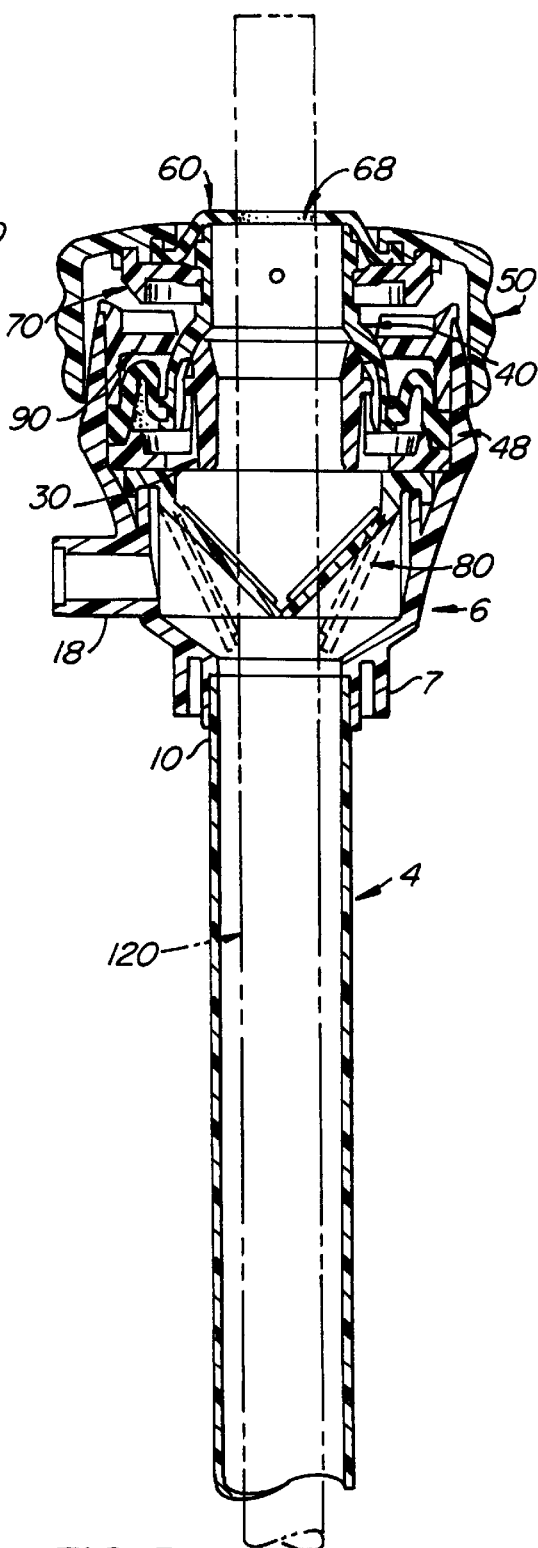
FIG. 3 is a cross-sectional view of the trocar assembly of FIG. 1, illustrating a 12 mm instrument passing through the valve assembly.

Referring to FIGS. 1–3, the valve assembly 8 of the present invention will now be described in detail. Valve assembly 8 generally comprises a pivot base 30 disposed within cavity 16 of handle 6, and a first valve member or pivot tower 40 pivotally coupled to base 30. A second valve member or dialator ring 50 is movably coupled around pivot tower 40. A flexible membrane seal 60 is retained between pivot tower 40 and dialator ring 50 by a seal retainer 70 for sealingly receiving elongated instruments of various cross-sectional shapes and sizes (discussed in detail below). Valve assembly 8 further includes a one-way sealing valve 80 positioned within cavity 16 distal to pivot base 30 for allowing elongate objects to pass through in the distal direction and for sealing cavity 16 when it is empty (e.g., during a change of instruments or after removing the access device(s)).

As shown in FIG. 2, pivot base 30 defines an inner passage 32 and an annular flange 34 fixed to an inner surface 35 of handle 6. Pivot tower 40 comprises an upper, cylindrical portion 42 engaged with membrane 60 and a lower flared portion 44 movably disposed between base 30 and an annular retainer 90. Retainer 90 includes an outer portion 91 fixed to the inner surface 35 of handle 6 around tower 40 and an inner projection 92 extending into the center of cavity 16. Flared portion 44 of pivot tower 40 is slidable between projection 92 and the outer surface of base 30. As shown in FIG. 3, projection 92 will prevent further pivoting of tower 40 when upper portion 42 of tower 40 engages projection 92. Preferably, tower 40 is capable of pivoting in any direction (i.e., 360°) around base 30 to ensure that an elongated object remains centered within valve assembly 8 (discussed below).

Referring again to FIG. 2, pivot tower 40 defines an annular groove 46 in flared portion 44 for receiving a pivot seal 48. Pivot seal 48 is preferably a flexible, elastomeric membrane having an outer circumferential edge 96 fixed to the inner surface of handle 6 and an inner circumferential edge 98 disposed within groove 46. As shown in FIG. 3, pivot seal 48 moves with pivot tower 40 as it rotates around base 30 to provide a fluid seal between tower 40 and the inner surface 35 of handle 6.

Dialator ring 50 is an annular collar defining a proximal opening 52 having a diameter larger than the largest object that will be received by introducer assembly 2 (i.e., at least 12 mm). As shown in FIG. 2, dialator ring 50 has an internal surface 54 with inner and outer grooves 56, 58 for receiving membrane 60 and seal retainer 70, respectively. Seal retainer 70 has an outer portion 72 disposed within outer groove 58 and an inner thread 74 threadably coupled to outer threads 100 on upper portion 42 of pivot tower 40. As shown in FIG. 1, outer threads 100 preferably have a spiral shape so that rotation of seal retainer 70 through threads 100 causes axial translation of retainer 70 relative to tower 40. Dialator ring 50 further defines an outer gripping surface 59 for facilitating handling by the surgeon. In this manner, the surgeon can grip surface 59 and rotate ring 50 (and retainer 70 therewith) to axially move ring 50 and retainer 70 relative to tower 40.

Membrane 60 is an annular, elastomeric seal defining a central aperture 62 aligned with the center of opening 52 of dialator ring 50. Membrane 60 is fabricated from a material which is sufficiently resilient to accommodate and provide a fluid seal with instruments of varying diameters, e.g., diameters of from 5 mm to 12 mm. As shown in FIG. 2, membrane 60 includes an outer edge 66 coupled within inner groove 56 of ring 50 and an inner portion 68 disposed across an upper surface 64 of pivot tower 40 to cover the outer portion of proximal opening 52. Axial movement of ring 50 relative to tower 40 will cause membrane 60 to stretch or relax, thereby changing the area of aperture 62 without substantially changing its circular shape.

Membrane 60 is movable between a first configuration (FIG. 2), in which membrane 60 is relaxed and aperture 62 has a relatively small area, and a second configuration (FIG. 3), in which membrane 60 is pulled downward and stretched so that aperture 62 has a relatively large area. Specifically, proximal movement of ring 50 relative to tower 40 moves membrane 60 towards the first configuration and vice versa. Of course, membrane 60 may also be moved to a variety of intermediate positions between the first and second configurations. In the preferred embodiment, aperture 62 has a diameter of about 5 mm in the first configuration and about 12 mm in the second configuration.

Referring to FIG. 2, one-way seal valve 80 is preferably a conical elastomeric membrane, such as a duckbill valve, having an outer flange 82 disposed between flange 34 of base 30 and a notch 84 within cavity 16 of handle 6. Valve 80 is biased inward to provide a fluid seal for cavity 16 both when an elongate object extends through cavity 16 and when no object is present in cavity 16. Of course, other conventional valves can be used for this purpose. For example, a septum valve (not shown) having a preformed puncture or crossed slits for receiving the elongated object can be used instead of a duckbill valve.

The method of the present invention for accommodating and providing a seal for various endoscopic instruments will now be described. Prior to introducing a surgical instrument or viewing scope, an obturator, insufflation needle or similar access device will be used to create a percutaneous penetration in the patient and to withdraw or introduce fluids into a body cavity. For example, in laparoscopic surgery, the insufflation needle will insufflate the abdominal cavity. When the access device is removed from introducer assembly 2, one-way seal valve 80 closes to prevent the escape of gas or other fluids from the abdomen. The surgeon then rotates dialator ring 50 until aperture 62 of membrane 60 has a diameter that corresponds to the instrument or scope that will be inserted through introducer assembly 2 (i.e., a diameter slightly less than the instrument to provide a suitable fluid seal around its periphery). For example, if the surgeon desires to use a 5 mm instrument 110 (see FIG. 2), ring 50 is rotated in the proximal direction until membrane 60 is completely relaxed and aperture 62 has a diameter of about 2.5 mm. The surgeon then introduces the instrument 110 through aperture 62, passage 32 of base 30, seal valve 80 and axial lumen 14 of cannula 4. Valve 80 and membrane 60 provide a suitable seal against the instrument's periphery during the surgical procedure.

When the surgeon desires to change the instrument 110, it is removed from introducer assembly 2 and ring 50 is rotated to a different discrete setting. For example, if the surgeon needs to use a 10 mm instrument 120 (see FIG. 3), ring 50 is rotated in the distal direction, thereby stretching membrane 60 and increasing the area of aperture 62, until aperture has an area slightly less than 10 mm or about 7 mm. The surgeon then introduces the 10 mm instrument 120 through aperture 62 as described above. Membrane 60 will provide an effective fluid seal in both configurations (FIGS. 2 and 3). In addition, since membrane 60 has been moved into the larger configuration by the valve assembly (and not the instrument itself as in many prior art sealing members), the frictional resistance applied to the 10 mm instrument 120 is substantially the same as the frictional resistance applied to the 5 mm instrument 110.

Figure 4:
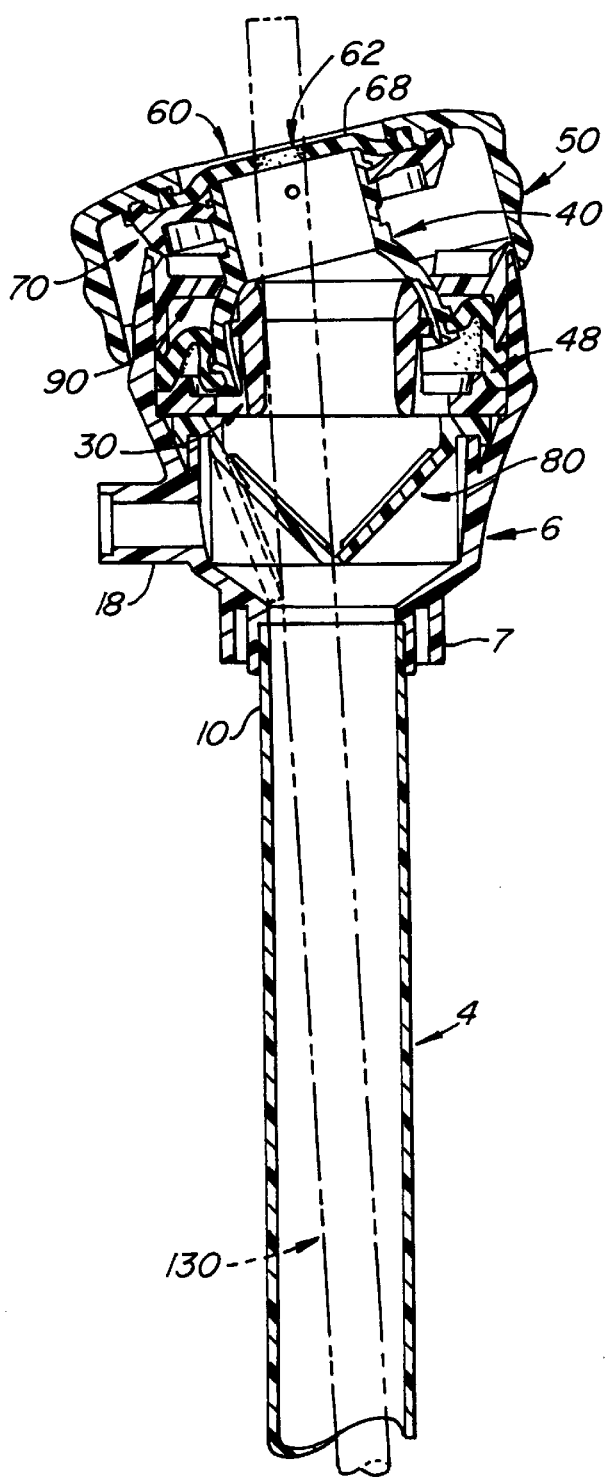
FIG. 4 is a cross-sectional view of the trocar assembly of FIG. 2, illustrating pivotal movement of the valve assembly relative to the trocar shaft in response to transverse deflection of the instrument.

During the surgical procedure, the surgeon will typically manipulate the instrument within the body cavity. Since introducer assembly 2 is designed to receive a wide variety of instrument sizes, many (if not all) of the instruments will have a smaller diameter than the inner diameter of axial lumen 14. Thus, as the instrument 130 is manipulated, it may move transversely or pivot within axial lumen 14 of cannula 4 (see FIG. 4). This transverse or pivotal movement of instrument 130 generates lateral pressure against membrane 60, which could result in fluid leakage between the instrument 130 and membrane 60. To prevent this from occurring, ring 50 and membrane 60 are pivotally coupled to base 30 and cannula 4, as described above. Consequently, when the instrument 130 pivots or moves relative to axial lumen 14 of cannula 4, ring 50 and membrane 60 will pivot with the instrument so that the instrument 130 remains in the center of opening 52. This reduces the lateral pressure against membrane 60 and minimizes fluid leakage through aperture 62.

Figure 5A:
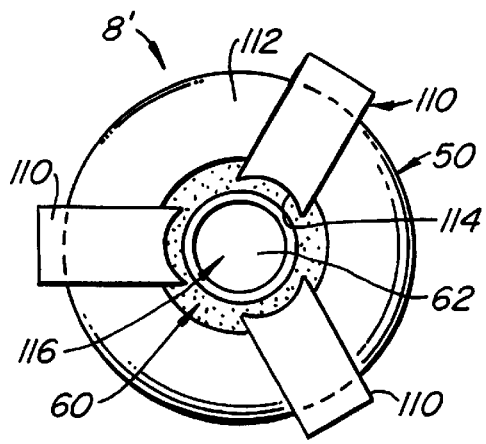
FIGS. 5A and 5B are top views of a representative trocar incorporating an alternative embodiment of the valve assembly of FIG. 1, illustrating the valve assembly sized for accommodating a 5 mm and a 12 mm instrument, respectively.
Figure 5B:
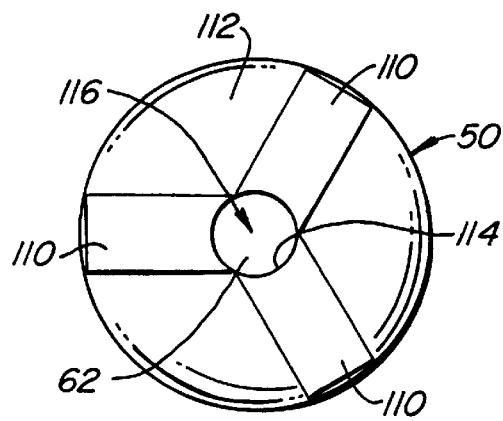

Although the foregoing invention has been described in detail for purposes of clarity, it will be obvious that certain modifications may be practiced within the scope of the appended claims. For example, the means for preventing transverse movement of the instrument relative to membrane 60 is not limited to the configuration described above. The instrument may be transversely fixed to membrane 60 rather than allowing the membrane to move with the instrument as described above in the preferred embodiment. A specific configuration of this concept is schematically illustrated in FIGS. 5A and 5B. As shown, valve assembly 8' includes a plurality of holding members 110 suitably coupled to the proximal surface 112 of dialator ring 50 for securing the instrument at or near the center of membrane 60. The holding members 110 extend radially inward and have inner ends 114 defining a central opening 116 therebetween. Inner ends 114 preferably have an arcuate shape that is complementary to the outer surface of an instrument shaft.

Holding members 110 are movable from a first configuration (FIG. 5B), in which the central opening 116 is relatively small, and second configuration (FIG. 5A), in which central opening 116 is relatively large. Holding members 110 will be moved so that opening 116 substantially corresponds to the outer diameter of the instrument passing therethrough. In a preferred configuration, holding members 110 are slidable along a track or groove (not shown) in the proximal surface of ring 50 for movement between the first and second configurations. Holding members 110 are biased radially inward by a suitable biasing means, such as a spring, so that members 110 secure the instrument at the center of membrane 60. Alternatively, holding members 110 may be manually moved by the surgeon, or they may be actuated by movement of ring 50 so that the size of central opening 116 corresponds to the size of aperture 62.

What is claimed is:

1. A introducer assembly for introducing elongate objects through a percutaneous penetration in a patient, the introducer assembly comprising:

an elongate shaft having proximal and distal ends and an axial lumen therebetween; and a valve assembly pivotally coupled to the proximal end of the shaft, the valve assembly comprising:

a first valve member defining an inner lumen for receiving elongated objects;

a flexible membrane defining an aperture positioned in general alignment with the inner lumen; and a second valve member coupled to the membrane for moving the membrane between a first configuration, in which the aperture has a first area, and a second configuration, in which the aperture has a second area not equal to the first area so to sealingly receive elongated objects having different cross-sectional areas, wherein the second valve member is positioned radially outward from the inner lumen of the first valve member, and wherein said valve assembly pivots in response to transverse movement of an elongate object within the axial lumen of the shaft.

2. The introducer assembly of claim 1 further comprising a hub attached to the proximal end of the shaft, the first and second valve members being pivotally coupled to the hub.

3. The introducer assembly of claim 2 wherein the first and second valve members are gimballed to the hub for 360 degree pivotal movement about a plane transverse to the axial lumen of the shaft.

4. The introducer assembly of claim 1 further comprising a plurality of holding members coupled to the first valve member, the holding members each having ends facing each other to define a gap therebetween for receiving the elongated object.

5. The introducer assembly of claim 4 wherein the holding members are movable between a first position, in which the gap has a first area, and a second position, in which the gap has a second area larger than the first area.

6. A valve for sealingly receiving elongated objects, the valve comprising:

a valve body defining an inner lumen for receiving elongated objects;

a flexible membrane defining an aperture substantially aligned with the inner lumen, the aperture defining an area; and a valve member threadably coupled to the valve body for varying the area of the aperture so to sealingly receive elongated objects having different cross-sectional areas, wherein the valve member is rotatable to axially translate said valve member relative to the body and is non-responsive to elongated objects passing through the inner lumen of the valve body.

7. The valve of claim 6 wherein the membrane is movable between a first configuration, in which the aperture has a first area for receiving a first elongated object with a first diameter, and a second configuration, in which the aperture has a second area for receiving a second elongated object with a second diameter not equal to the first diameter.

8. The valve of claim 7 wherein the aperture, in the first configuration, has a diameter of about 4 to 6 mm and, in the second configuration, has a diameter of about 11 to 13 mm.

9. The valve of claim 7 wherein the aperture has substantially the same shape in the first and second configurations.

10. The valve of claim 9 wherein the aperture is substantially circular.

11. The valve of claim 7 wherein the membrane offers a substantially equivalent frictional resistance to the first and second elongated objects in the first and second configurations, respectively.

12. The valve of claim 7 wherein the diameter of the aperture in the first and second configurations is slightly less than the diameter of the first and second elongated objects, respectively.

13. The valve of claim 6 wherein the flexible membrane is an annular membrane comprising an elastomeric material.

14. A pneumostasis valve for introduction of elongated objects into a patient's body, the valve comprising:

a hollow tube defining an inner lumen with a proximal opening for receiving the elongated object;

a flexible membrane defining an aperture positioned over the proximal opening and substantially aligned with the inner lumen; and a collar threadably secured to axially translate over the hollow tube and coupled to an outer edge of the flexible membrane, wherein the collar is rotatable to cause axial translation of the collar relative to the hollow tube and wherein distal movement of the collar relative to the hollow tube causes the aperture to open radially outward and proximal movement of the collar causes the aperture to close radially inward.

15. The valve of claim 14 wherein the flexible membrane is a thin, resilient membrane comprising an elastomeric material.

16. A method for introducing elongated objects into a patient's body, the method comprising:

providing a valve body having an opening for receiving elongated objects and a flexible membrane with an aperture substantially aligned with the opening;

rotating a collar threadably coupled to the valve body to move the collar in a distal direction relative to the valve body, the collar being coupled to an outer portion of the membrane in order to stretch the membrane radially outward from a center of the proximal opening of the hollow tube to enlarge the diameter of the aperture; and after the rotating step, introducing an elongated object through the aperture and the flexible membrane into the patient's body.

17. The method of claim 16 wherein the aperture, in a first configuration, has a diameter of about 4 to 6 mm and, in a second configuration, has a diameter of about 11 to 13 mm.

18. The method of claim 17 further comprising offering substantially the same frictional resistance to elongated objects extending through the flexible membrane in the first and second configurations.

19. The method of claim 17 wherein the aperture retains substantially the same shape as it is stretched.

20. The method of claim 16 wherein the aperture is circular.

21. A method for introducing elongated objects into a patient's body comprising:

introducing a first elongated object having a first diameter through an opening in a valve body and an aperture of a flexible membrane and into the patient's body;

manipulating the first elongated object so that said object moves transversely relative to the valve body, wherein the membrane is pivotally attached to the valve body to allow the membrane to pivot in response to movement of said object;

removing the first elongated object;

enlarging the aperture; and after the enlarging step introducing a second elongated object having a second diameter through the opening and the aperture and into the patient's body, the second diameter being larger than the first diameter.

22. The method of claim 21 wherein the first diameter is about 4–6 mm and the second diameter is about 10–15 mm.

23. The method of claim 21 wherein the enlarging step comprises moving an outer portion of the membrane in the distal direction to stretch an inner portion of the membrane radially outward and thereby enlarge the aperture.

\* \* \* \* \*